United States Patent
Chung

(10) Patent No.: US 12,311,248 B2
(45) Date of Patent: May 27, 2025

(54) METHOD AND SYSTEM FOR MOVEMENT GUIDANCE, ELECTRONIC DEVICE AND SERVER

(71) Applicant: CHAMP VISION DISPLAY INC., Miao-Li County (TW)

(72) Inventor: Hsin-Mao Chung, Miao-Li County (TW)

(73) Assignee: CHAMP VISION DISPLAY INC., Miao-Li County (TW)

( * ) Notice: Subject to any disclaimer, the term of this patent is extended or adjusted under 35 U.S.C. 154(b) by 16 days.

(21) Appl. No.: 18/322,601

(22) Filed: May 24, 2023

(65) Prior Publication Data

US 2023/0381628 A1 Nov. 30, 2023

(30) Foreign Application Priority Data

May 30, 2022 (TW) .................................. 111120032

(51) Int. Cl.
*A61B 5/11* (2006.01)
*A63B 71/06* (2006.01)

(52) U.S. Cl.
CPC ........ *A63B 71/0622* (2013.01); *A61B 5/1126* (2013.01); *A63B 2071/0625* (2013.01); *A63B 2071/0647* (2013.01); *A63B 2214/00* (2020.08); *A63B 2220/802* (2013.01); *A63B 2220/836* (2013.01)

(58) Field of Classification Search
CPC .......................... A61B 5/1126; A63B 71/0622
See application file for complete search history.

(56) References Cited

FOREIGN PATENT DOCUMENTS

| | | |
|---|---|---|
| CN | 201492862 | 6/2010 |
| CN | 105879357 | 8/2016 |
| CN | 108853946 | 11/2018 |
| CN | 111541938 | 8/2020 |
| CN | 112823044 | 5/2021 |
| CN | 113144542 | 7/2021 |
| TW | 202036234 | 10/2020 |
| TW | I739551 | 9/2021 |
| TW | M622555 | 1/2022 |

*Primary Examiner* — Kesha Frisby
(74) *Attorney, Agent, or Firm* — JCIPRNET

(57) ABSTRACT

A method and system for movement guidance, an electronic device, and a server are disclosed. The method includes: receiving a first ultrasound signal from a first ultrasound emission device via a first sound reception device and receiving a background sound signal via the first sound reception device synchronously, wherein the first ultrasound emission device is worn on a body of a first user; generating a multimedia file according to the first ultrasound signal and the background sound signal; detecting a first signal feature of the first ultrasound signal, wherein the first signal feature reflects a first physical movement performed by the first user at a first time point; and generating a first guidance message according to the first signal feature, wherein the first guidance message is used for guiding a second user to perform the first physical movement at a second time point.

13 Claims, 5 Drawing Sheets

METHOD AND SYSTEM FOR MOVEMENT GUIDANCE, ELECTRONIC DEVICE AND SERVER

CROSS-REFERENCE TO RELATED APPLICATION

This application claims the priority benefit of Taiwan application serial no. 111120032, filed on May 30, 2022. The entirety of the above-mentioned patent application is hereby incorporated by reference herein and made a part of this specification.

BACKGROUND OF THE INVENTION

Field of the Invention

The invention relates to a method and a system for movement guidance, an electronic device, and a server.

Description of Related Art

With the advancement of technology and disease prevention, home office and learning have gradually become a trend, and the fitness industry is also continuously developing online coaching platforms to assist people in self-training at home. However, issues that online coaching platforms are prone to encounter include excessive cost of recording and post-production of teaching videos, higher requirements for video equipment on the student side, and difficulty of communicating feedback from coaches in real time. Therefore, the results of the online coaching platforms for home fitness are not satisfactory and the platforms may not be promoted smoothly.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the invention was acknowledged by a person of ordinary skill in the art.

SUMMARY OF THE INVENTION

Accordingly, the invention provides a method and a system for movement guidance, an electronic device, and a server that may improve the convenience for coaches to guide the remote movements of students.

An embodiment of the invention provides a method for movement guidance, including: receiving a first ultrasound signal emitted by at least one first ultrasound emission device via at least one first sound reception device, and simultaneously receiving a background sound signal via the at least one first sound reception device, wherein the at least one first ultrasound emission device is worn on a body of a first user; generating a multimedia file according to the first ultrasound signal and the background sound signal; detecting a first signal feature of the first ultrasound signal, wherein the first signal feature reflects a first physical movement performed by the first user at a first time point; and generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

In an embodiment of the invention, the first signal feature includes a spectral feature of the first ultrasound signal.

In an embodiment of the invention, the step of generating the first guidance message according to the first signal feature includes: determining that the first physical movement performed by the first user at the first time point is a first movement in response to the first signal feature meeting a first condition; and determining that the first physical movement performed by the first user at the first time point is a second movement in response to the first signal feature meeting a second condition, wherein the first condition is different from the second condition, and the first movement is different from the second movement.

In an embodiment of the invention, the at least one first ultrasound emitter includes a first ultrasound emitter and a second ultrasound emitter, the first ultrasound emitter and the second ultrasound emitter are worn at different positions on the body of the first user, the first ultrasound emitter is used for emitting an ultrasound signal having a first frequency, the second ultrasound emitter is used for emitting an ultrasound signal having a second frequency, and the first frequency is different from the second frequency.

In an embodiment of the invention, the method for movement guidance further includes: detecting a second signal feature of the first ultrasound signal, wherein the second signal feature reflects a change in a position of the first user in a physical space; and generating a second guidance message according to the second signal feature, wherein the second guidance message is used for guiding the second user to move in a specific direction.

In an embodiment of the invention, the second signal feature includes an amplitude feature of the first ultrasound signal.

In an embodiment of the invention, the step of generating the second guidance message according to the second signal feature includes: tracking a movement trajectory of the first user in the physical space according to the second signal feature; and generating the second guidance message according to the movement trajectory.

In an embodiment of the invention, the method for movement guidance further includes: outputting the first guidance message via a signal output device based on at least one form of a sound and an image when the movement teaching file is played, so as to guide the second user to perform the first physical movement at the second time point via the first guidance message.

In an embodiment of the invention, the method for movement guidance further includes: receiving a second ultrasound signal emitted by at least one second ultrasound emission device via at least one second sound reception device when the movement teaching file is played, wherein the at least one second ultrasound emission device is worn on a body of the second user; detecting a third signal feature of the second ultrasound signal, wherein the third signal feature reflects a second physical movement performed by the second user at the second time point; and generating third guidance information according to the third signal feature, wherein the third guidance information is used for assisting the second user to evaluate a correctness of the second physical movement.

In an embodiment of the invention, the method for movement guidance further includes: filtering out information of the first ultrasound signal from the movement teaching file before the movement teaching file is played; and playing the filtered movement teaching file after the information of the first ultrasound signal is filtered out from the multimedia file.

An embodiment of the invention further provides a system for movement guidance, including at least one first ultrasound emission device, at least one first sound reception device, and a processor. The at least one first ultrasound emission device is suitable to be worn on a body of a first user and used for emitting a first ultrasound signal. The at least one first sound reception device is used for receiving the first ultrasound signal and a background sound signal. The processor is coupled to the at least one first sound reception device and used for: generating a multimedia file according to the first ultrasound signal and the background sound signal; detecting a first signal feature of the first ultrasound signal, wherein the first signal feature reflects a first physic al movement performed by the first user at a first time point; and generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

An embodiment of the invention further provides an electronic device, including at least one first sound reception device and a processor. The at least one first sound reception device is used for receiving a first ultrasound signal emitted by at least one first ultrasound emission device and synchronously receiving a background sound signal. The at least one first ultrasound emission device is worn on a body of a first user. The processor is coupled to the at least one first sound reception device and used for: generating a multimedia file according to the first ultrasound signal and the background sound signal; detecting a first signal feature of the first ultrasound signal, wherein the first signal feature reflects a first physical movement performed by the first user at a first time point; and generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

An embodiment of the invention further provides a server including a communication interface and a processor. The communication interface is used for communicating with at least one first sound reception device. The processor is coupled to the communication interface. The at least one first sound reception device is used for receiving a first ultrasound signal emitted by at least one first ultrasound emission device and synchronously receiving a background sound signal, and transmitting the first ultrasound signal and the background sound signal to the processor via the communication interface. The at least one first ultrasound emission device is worn on a body of a first user. The processor is used for: generating a multimedia file according to the first ultrasound signal and the background sound signal; and detecting a first signal feature of the first ultrasound signal, wherein the first signal feature reflects a first physical movement performed by the first user at a first time point; and generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

Based on the above, after the first ultrasound signal emitted by the ultrasound emission device worn on the body of the first user and the background sound signal are received via the sound reception device, the multimedia file may be automatically generated according to the first ultrasound signal and the background sound signal. Moreover, the first signal feature of the first ultrasound signal may be detected to reflect the first physical movement performed by the first user at the first time point, and the first guidance message may be automatically generated according to the first signal feature and added to the multimedia file to generate the movement teaching file. In particular, the first guidance message may be used for guiding the second user to perform the first physical movement at the second time point. In this way, the convenience for the coach to guide the remote movement of the student may be effectively improved.

Other objectives, features and advantages of the present invention will be further understood from the further technological features disclosed by the embodiments of the present invention wherein there are shown and described preferred embodiments of this invention, simply by way of illustration of modes best suited to carry out the invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

It is to be understood that other embodiment may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

Figure 1:
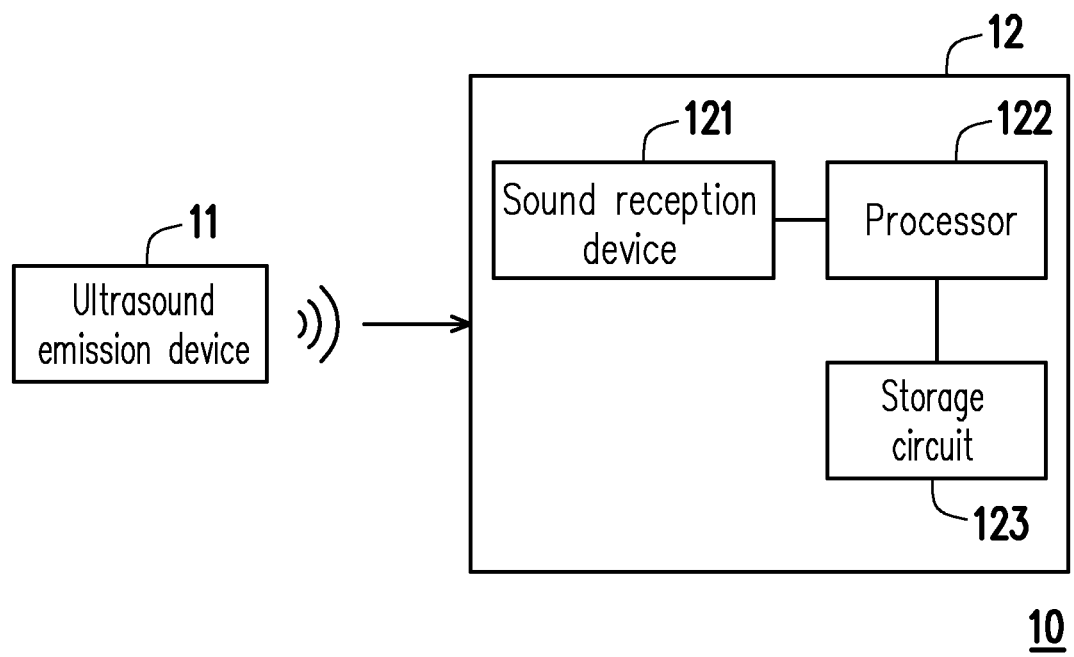
FIG. 1 is a schematic diagram of a system for movement guidance according to an embodiment of the invention.

FIG. 1 is a schematic diagram of a system for movement guidance according to an embodiment of the invention. Referring to FIG. 1, a system 10 for movement guidance includes an ultrasound emission device (also referred to as a first ultrasound emission device) 11 and an electronic device 12. The ultrasound emission device 11 is suitable for being worn on the body of a user (also referred to as a first user) and used for emitting an ultrasound signal (also referred to as a first ultrasound signal). For example, the ultrasound emission device 11 may include one or a plurality of ultrasound emitters. Each ultrasound emitter may be used for emitting an ultrasound signal with a specific frequency (fixed frequency). For example, the specific frequency may be 30,000 Hz (i.e., 30 kHz), and the invention is not limited thereto. For example, in an embodiment, the specific frequency may also include 29 kHz or 31 kHz, as long as the specific frequency is higher than the frequency of the sound signal that may be heard by the human ear (for example, a frequency higher than 20 kHz or higher than 25 kHz).

In an embodiment, assuming that the ultrasound emission device 11 includes a plurality of ultrasound emitters, these ultrasound emitters may be used for emitting ultrasound signals having different frequencies. For example, the ultrasound emission device 11 may include a first ultrasound emitter and a second ultrasound emitter. The first ultrasound emitter may be used for emitting an ultrasound signal having a specific frequency (also referred to as a first frequency). The second ultrasound emitter is used for emitting an ultrasound signal having another specific frequency (also referred to as a second frequency). The first frequency is different from the second frequency. For example, the first frequency and the second frequency may be 30 kHz and 31 kHz, respectively, and the actual values of the first frequency and the second frequency are not limited thereto.

In an embodiment, the plurality of ultrasound emitters (e.g., the first ultrasound emitter and the second ultrasound emitter) of the ultrasound emission device 11 are suitable to be worn on different positions on the body of the user (i.e., the first user). For example, the first ultrasound emitter may be worn on the left arm of the first user, and the second ultrasound emitter may be worn on the right arm of the first user, etc., and the wearing positions of the plurality of ultrasound emitters on the body of the first user may also include other positions of the human body (e.g., thighs or calves, etc.), and the invention is not limited in this regard. Moreover, the ultrasound emission device 11 may further include more ultrasound emitters (e.g., a third ultrasound emitter, etc.), and the invention does not limit the total number of ultrasound emitters included in the ultrasound emission device 11.

The electronic device 12 may include various electronic devices having sound signal transceiver and data processing functions such as smartphones, tablets, laptops, desktops, game consoles, smart headphones, smart speakers, or smart TVs, and the type of the electronic device 12 is not limited thereto.

The electronic device 12 may include a sound reception device 121, a processor 122, and a storage circuit 123. The sound reception device 121 is used for receiving a first ultrasound signal. For example, the sound reception device 121 may include one or a plurality of microphones (e.g., a plurality of microphones may simultaneously receive the first ultrasound signal). In addition, during the period of receiving the first ultrasound signal, the sound reception device 121 may simultaneously receive a background sound signal. The background sound signal may reflect sounds audible to human ears in the current environment (e.g., music played in the current environment). For example, the frequency of the background sound signal may be within an auditory frequency range (e.g., 20 Hz to 20 kHz), and the background sound signal may be generated by playing background music via an audio playing device such as a speaker in the environment. That is to say, assuming that both the first ultrasound signal and the background sound signal exist in the current environment where the sound reception device 121 is located, the sound reception device 121 may simultaneously receive (e.g., detect) the first ultrasound signal and the background sound signal. In particular, the background sound signal is, for example, background music or just ambient sound, and since the frequency bands of the background sound signal and the ultrasound signal are different, the two may be readily separated or synthesized. Therefore, the background sound signal synchronously received by the sound reception device 121 during recording may be retained in subsequent use, or may be filtered out and added with other background sounds (e.g., music selected by the second user).

The processor 122 is coupled to the sound reception device 121 and the storage circuit 123. The processor 122 is used for the whole or part of the operation of the electronic device 12. For example, the processor 122 may include a central processing unit (CPU) or other programmable microprocessors for conventional use or special use, a digital signal processor (DSP), a programmable controller, an application-specific integrated circuit (ASIC), a programmable logic device (PLD), other similar devices, or a combination of the devices.

The storage circuit 123 is used for storing data. For example, the storage circuit 123 may include a volatile storage circuit and a non-volatile storage circuit. The volatile storage circuit is used for volatile storage of data. For example, the volatile storage circuit may include random-access memory (RAM) or similar volatile storage media. The non-volatile storage circuit is used for non-volatile storage of data. For example, the non-volatile storage circuit may include read-only memory (ROM), solid-state disk (SSD), conventional hard disk drive (HDD), or similar non-volatile storage media.

In an embodiment, the electronic device 12 may further include a power management circuit and various input/output (I/O) devices. For example, the power management circuit may be used for managing the power of the electronic device 12. The I/O device may be used for inputting and outputting a signal. For example, the I/O device may include a communication interface (such as a network interface card), a display interface (such as a screen), a control interface (such as a keyboard and a mouse), and an audio output interface (such as a speaker), and the type of the I/O device is not limited thereto.

Further, after the first ultrasound signal and the background sound signal are received by the electronic device 12, the processor 122 may generate a multimedia file according to the first ultrasound signal and the background sound signal, and the multimedia file is an audio file. For example, the multimedia file may carry at least part of the signal feature of the first ultrasound signal and the background sound signal. Then, the multimedia file may be used for separating and outputting the background sound signal, so as to play the background music corresponding to the background sound signal.

Moreover, the processor 122 may detect (analyze) the signal feature of the first ultrasound signal of the multimedia file to obtain a first signal feature. The first signal feature may reflect a specific physical movement (also referred to as a first physical movement) performed by the first user at a specific time point (also referred to as a first time point). The processor 122 may generate a guidance message (also referred to as a first guidance message) according to the first signal feature, and the first guidance message may be used for guiding another user (also referred to as a second user) to perform the first physical movement at another time point (also referred to as a second time point). The first time point is different from the second time point.

Moreover, the processor 122 may add the first guidance message to the multimedia file according to the first time point corresponding to the first signal feature (meaning that the ultrasound signal generated by the movement is converted into a guidance message, and the guidance message is, for example, a voice), to generate a new multimedia file (also known as a movement teaching file, and the first guidance message and the first signal feature are, for example, located (started) at the same time point of the new multimedia file). In particular, the movement teaching file may be played in the environment where the second user is located, so as to guide the second user to follow the first physical movement performed by the first user at the second time point to perform self-training.

In an embodiment, the first user is, for example, a coach and the second user is, for example, a learner. When the movement teaching file is played in the environment where the second user is located, the background sound signal may also be output to play background music. At the same time, during the playback of the background music, the first guidance message may be output at a suitable time point according to the time point (e.g., a time stamp) originally added in the multimedia file. According to the first guidance message, the second user may try to perform the first physical movement performed by the coach at a second time point.

Figure 2:
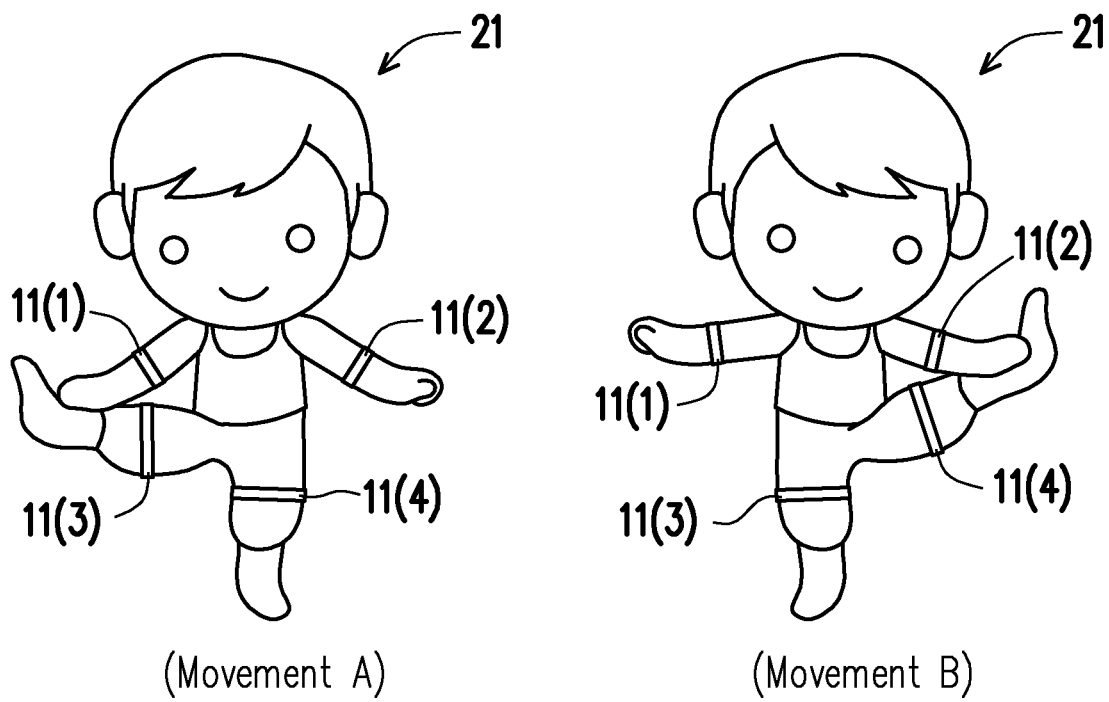
FIG. 2 is a schematic diagram of a user wearing an ultrasound emission device to perform different physical movements according to an embodiment of the invention.

FIG. 2 is a schematic diagram of a user wearing an ultrasound emission device to perform different physical movements according to an embodiment of the invention. Please refer to FIG. 1 and FIG. 2 at the same time, it is assumed that the ultrasound emission device 11 of FIG. 1 includes ultrasound emitters 11(1) to 11(4). The ultrasound emitters 11(1) to 11(4) may be respectively worn on the right arm, the left arm, the right thigh, and the left thigh of a user (i.e., the first user) 21. The ultrasound emitters 11(1) to 11(4) may be used for emitting ultrasound signals (i.e., a first ultrasound signal), and the (preset) frequencies of the ultrasound signals emitted by the ultrasound emitters 11(1) to 11(4) are different from each other.

When the user 21 performs movement A (for example, raising both hands and raising the right thigh), the signal features (i.e., the first signal features) of the ultrasound signals emitted by the ultrasound emitters 11(1) to 11(4) may jointly form the signal features corresponding to movement A. Moreover, when the user 21 performs movement B (for example, raising both hands and raising the left thigh), the signal features (i.e., the first signal features) of the ultrasound signals emitted by the ultrasound emitters 11(1) to 11(4) may jointly form the signal features corresponding to movement B. In particular, movement A and movement B have different physical movements, and therefore the signal features corresponding to movement A are different from the signal features corresponding to movement B. Next, by (only) detecting (or analyzing) the signal features of the ultrasound signals emitted by the ultrasound emitters 11(1) to 11(4), the physical movements performed by the user 21 at a specific time point (i.e., the first time point) may be obtained.

In an embodiment, the first signal features may include spectral features of the first ultrasound signal. The spectral features of the first ultrasound signal may be used for describing the relative relationship between the frequency and time of the first ultrasound signal. Or, from another perspective, the spectral features of the first ultrasound signal may reflect the amount of variation of the frequency of the first ultrasound signal at different time points (for example, when the first user performs a movement, the ultrasound emission device 11 moves closer or farther away from the sound reception device 121, and the frequency is changed due to the Doppler effect). Taking FIG. 2 as an example, the spectral features of the first ultrasound signal corresponding to movement A are different from the spectral features of the first ultrasound signal corresponding to movement B. Therefore, by analyzing the spectral features of the ultrasound signals (the first ultrasound signal) emitted by the ultrasound emitters 11(1) to 11(4), whether the physical movement performed by the user 21 at a specific time point (i.e., the first time point) is movement A or movement B may be determined.

In an embodiment, in response to the first signal features meeting a certain condition (also referred to as a first condition), the processor 122 may determine that the first physical movement performed by the first user at the first time point is a specific movement (also referred to as a first movement, such as movement A). Or, in response to the first signal features meeting another condition (also referred to as a second condition), the processor 122 may determine that the first physical movement performed by the first user at the first time point is another movement (also referred to as a second movement, such as movement B). The first condition is different from the second condition, and the first movement is different from the second movement. When it is detected that the first signal features include signal features corresponding to movement A, the processor 122 may determine that the first physical movement performed by the first user at the first time point is movement A. Or, when it is detected that the first signal features include signal features corresponding to movement B, the processor 122 may determine that the first physical movement performed by the first user at the first time point is movement B. Moreover, it should be mentioned that, the positions where the user 21 wears the ultrasound emitters 11(1) to 11(4), the total number of the ultrasound emitters 11(1) to 11(4), and the physical movements (such as movement A and movement B) performed are all examples and are not intended to limit the invention.

Figure 3:
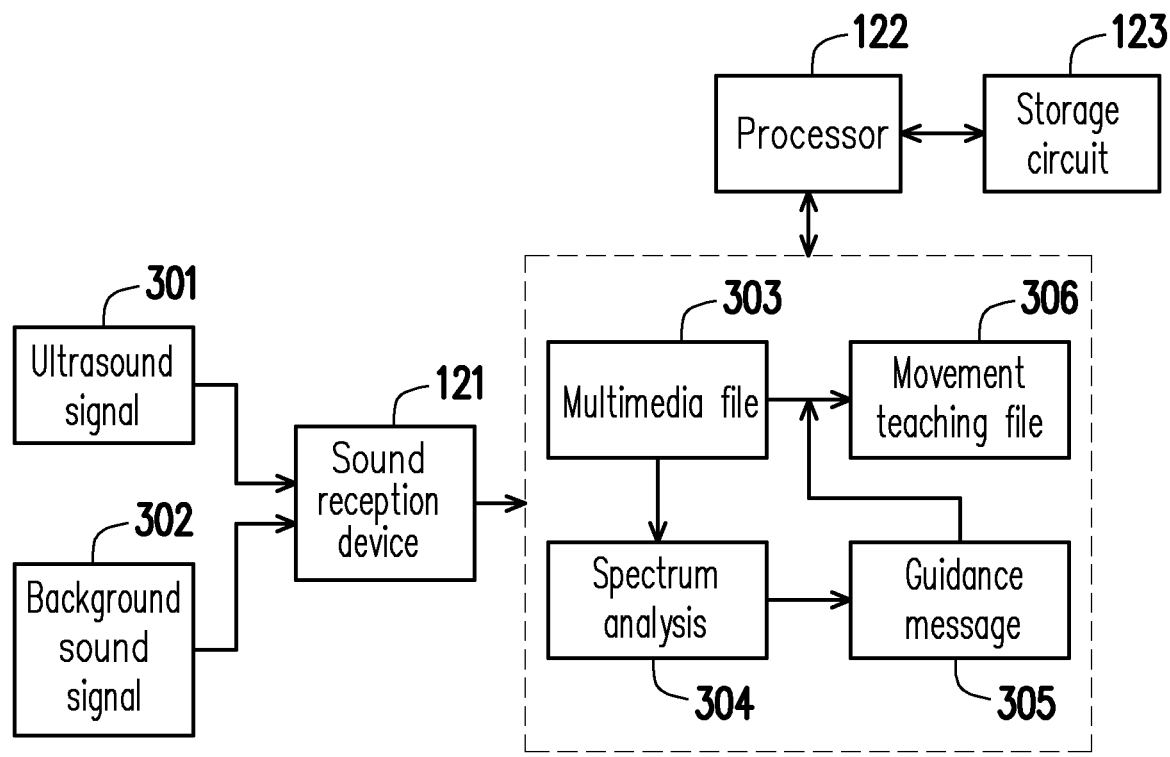
FIG. 3 is a schematic diagram of generating a movement teaching file according to an embodiment of the invention.

FIG. 3 is a schematic diagram of generating a movement teaching file according to an embodiment of the invention. Referring to FIG. 3, after an ultrasound signal 301 (i.e., the first ultrasound signal) and a background sound signal 302 are received via the sound reception device 121, the processor 122 may generate a multimedia file 303 according to the ultrasound signal 301 and the background sound signal 302. The multimedia file 303 may contain signal features (e.g., spectral features) or signal content of the ultrasound signal 301 and the background sound signal 302. The multimedia file 303 is stored in a temporary storage circuit or the storage circuit 123, for example, and the invention is not particularly limited in this regard. In particular, in FIG. 3, the multimedia file 303, a spectrum analysis 304, a guidance message 305, and a movement teaching file 306 shown in the dotted box are actions performed by the processor 122 or files stored in the storage circuit 123 (or other temporary storage circuits), wherein the actions performed by the processor 122 may be implemented by programs or by physical circuits.

The processor 122 may perform the spectrum analysis 304 on the ultrasound signal 301 of the multimedia file 303 to generate the guidance message 305. In the spectrum analysis 304, the processor 122 may generate the guidance message 305 according to the spectral features (i.e., the first signal features) of the ultrasound signal 301. For example, the processor 122 may identify the first physical movement performed by the first user at the first time point according to the spectral features of the ultrasound signal 301 to obtain an identification result (e.g., a specific physical movement or signal feature). The processor 122 may extract a guidance message from the storage circuit 123 as the guidance message 305 according to the identification result.

In an embodiment, the storage circuit 123 may store guidance messages corresponding to different physical movements or signal features. For example, assuming that the identification result of the first physical movement reflects that the first physical movement is "push-up", the guidance message 305 may include "perform push-up after seconds", "perform push-up" or similar guidance messages that may be used for guiding the second user to perform push-ups. Or, assuming that the identification result of the first physical movement reflects that the first physical movement is "sit-up", the guidance message 305 may include "perform sit-up after 5 seconds", "perform sit-up" or similar guidance messages that may be used for guiding the second user to perform sit-ups. Moreover, in an embodiment, the processor 122 may also directly extract a guidance message from the storage circuit 123 as the guidance message 305 according to the spectral features (i.e., the first signal features) of the ultrasound signal 301.

After the guidance message 305 is obtained, the processor 122 may add the guidance message 305 to the multimedia file 303 according to the time point (i.e., the first time point) corresponding to the first signal features to generate the movement teaching file 306 carrying the guidance message 305. For example, the first time point may refer to a time point at which the first user performs the first physical movement (that is, the movement performed by the first user at a specific time during the recording period of the multimedia file 303).

In an embodiment, the first time point corresponds to a specific time stamp (also referred to as a first time stamp) in the multimedia file 303. For example, in the process of generating (e.g., recording) the multimedia file 303 according to the ultrasound signal 301 and the background sound signal 302, according to the time point (i.e., the first time point) when the first signal features (or the first physical movement) are detected, the corresponding time stamp (i.e., the first time stamp) in the multimedia file 303 may be recorded. Then, the processor 122 may add the guidance message 305 to the multimedia file 303 according to the first time stamp to generate the movement teaching file 306 carrying the guidance message 305. It is particularly noted that the time period in which the sound is received by the sound reception device 121 and the movement teaching file 306 is generated by the processor 122 is, for example, a recording period.

Then, during the process of playing the movement teaching file 306, the guidance message 305 may be played synchronously with the background music at a suitable time point according to the first time stamp. For example, it is assumed that the time length of the movement teaching file 306 is 3 minutes, and the first time stamp is located at the 1st minute of the timeline of the movement teaching file 306 (that is, the coach performs the first physical movement when the background music is played to the 1st minute). During the period when the learner is performing self-training according to the played movement teaching file 306, when the movement teaching file 306 is about to play to the 1st minute in the timeline of the movement teaching file 306 (that is, before the background music is played to the 1st minute), the guidance message 305 may be output in advance (e.g., output the guidance message 305 when the background music is played to the 55th second) to guide the second user to prepare to perform the first physical movement at a second time point (e.g., after 5 seconds, the time is preset). For example, the guidance message 305 may be output in the form of sound or video. In addition, the movement teaching file 306 may be stored in the storage circuit 123 and may be shared or transmitted to other electronic devices for playback. Accordingly, even if the coach does not use a video recording medium to record the video footage when recording the teaching material, with the continuous playback of the movement teaching file of the invention, the learner may also accurately perform corresponding self-training with the assistance of background music and guidance messages. It should be mentioned that, the time length of the multimedia file 303 is, for example, the same as the time length of the movement teaching file 306, and the position of the first time stamp on the timeline of the multimedia file 303, for example, corresponds to the position of the second time stamp on the timeline of the movement teaching file 306 (e.g., the same timeline position, for example, both are at the 1st minute of the file). In other embodiments, a pre-file (such as prelude or pre-guidance sound) and/or a post-file may be added before and/or after the movement teaching file 306, and the pre-file and/or the post-file and the movement teaching file 306 may also be integrated into one teaching file, but the first time point and the second time point still correspond to each other on the timeline.

In an embodiment, the processor 122 may generate a first guidance signal according to the first signal features by means of feature comparison. For example, the processor 122 may compare the spectral features of the first ultrasound signal with a plurality of spectrum models in the database of the storage circuit 123. If the spectral features of the first ultrasound signal match a specific spectrum model (e.g., the first signal features meet the first condition or the second condition), the processor 122 may set the guidance message corresponding to the spectrum model as the first guidance message.

In an embodiment, the processor 122 may generate the first guidance signal according to the first signal features via an artificial intelligence (AI) model. For example, the AI model may be implemented via a neural network architecture and/or a deep learning network architecture such as Multilayer Perceptron, Deep Neural Network (DNN), Convolutional Neural Network (CNN), Recurrent Neural Network (RNN), and the invention is not limited in this regard. By training a classifier in the AI model, the trained classifier may generate one classification result according to the first signal features. The classification result may reflect whether the first signal features meet certain conditions (e.g., the first condition and the second condition). According to the classification result, the processor 122 may generate a corresponding first guidance message.

Figure 4:
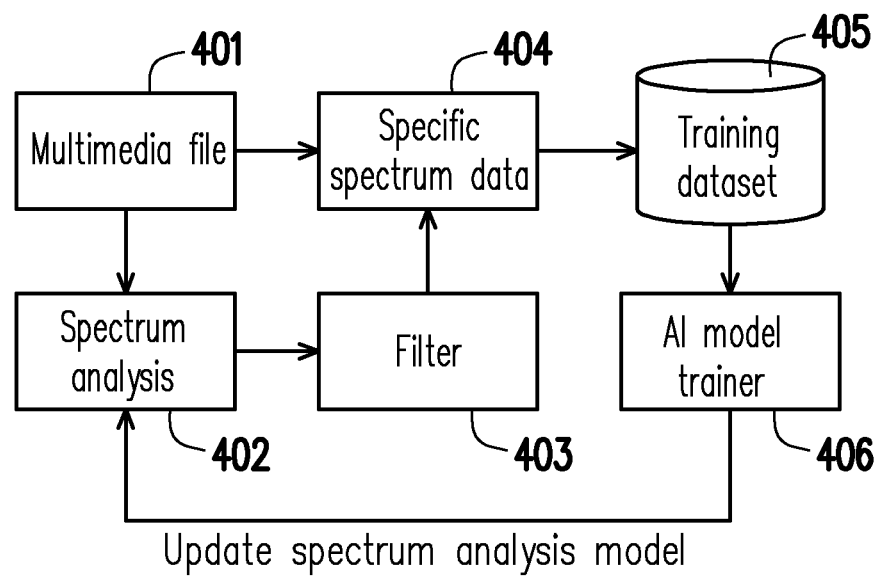
FIG. 4 is a schematic diagram of a training process of an AI model according to an embodiment of the invention.

FIG. 4 is a schematic diagram of a training process of an AI model according to an embodiment of the invention.

Referring to FIG. 4, the processor 122 may perform a spectrum analysis 402 on a multimedia file 401 as a training sample, so as to extract a specific spectrum data 404 within a specific time range from the multimedia file 401. The processor 122 may add the spectrum data 404 to a training dataset 405. An AI model trainer 406 may use the spectrum data 404 in the training dataset 405 to train the AI model, e.g., to update decision parameters (e.g., weight values) of the AI model. For example, assuming that the spectral data in a certain time range in the known multimedia file 401 includes the spectral data of the ultrasound signal generated by the coach performing a specific movement (for example, movement A of FIG. 2), the spectral data in this time range may be used for training the classifier in the AI model to automatically find the spectral features corresponding to movement A. Then, when the ultrasound signals input to this AI model have the same or similar spectral features, the classifier in the AI model may automatically determine that the ultrasound signals correspond to movement A and generate a corresponding classification result.

In an embodiment, after the AI model learns the spectral features corresponding to movement A, the processor 122 may filter out the signal content in the multimedia file 401 having the spectral features corresponding to movement A via a filter 403, and add the spectral data contained in the remaining multimedia file as the spectral data 404 to the training dataset 405. Then, the training dataset 405 may be used for training the AI model to learn the spectral features of the ultrasound signals corresponding to other physical movements (e.g., movement B of FIG. 2). By learning the signal features of the ultrasound signals corresponding to various physical movements one by one, the types of physical movements that the AI model may identify may continue to increase.

In an embodiment, the total number of the sound reception device 121 may be a plurality, and the sound reception devices 121 may be distributed around the environment where the first user is located. According to the first ultrasound signal received by the plurality of sound reception devices 121, the processor 122 may detect another signal feature (also referred to as a second signal feature) of the first ultrasound signal. In particular, the second signal feature may be different from the first signal feature. For example, the second signal feature may reflect the position change of the first user in the physical space. The processor 122 may generate another guidance message (also referred to as a second guidance message) according to the second signal feature. For example, the second guidance message may be used for guiding the second user to move in a specific direction.

Taking FIG. 2 as an example, it is assumed that the first user also moves in a specific direction (e.g., moves to the left while performing movement A of FIG. 2) during the performance of the first physical movement. According to the second signal feature, the processor 122 may generate the second guidance message. For example, the second guidance message may include "move left" or a similar guidance message that may be used for guiding the second user to move in a specific direction.

In an embodiment of FIG. 3, the guidance message 305 may include the first guidance message and the second guidance message at the same time. Then, during the playback of the movement teaching file 306, the second guidance message may be output along with the first guidance message, in order to guide the second user to perform the first physical movement at the second time point and move in a specific direction (for example, move to the left while performing movement A of FIG. 2).

In an embodiment, the second signal feature includes an amplitude feature of the first ultrasound signal. The amplitude feature of the first ultrasound signal may be used for describing the relative relationship between amplitude (i.e., signal strength) and time of the first ultrasound signal. Or, from another perspective, the amplitude feature of the first ultrasound signal may reflect the amount of variation of the amplitude of the first ultrasound signal between different time points.

For example, the processor 122 may define the movement trajectory of the first user in the physical space according to the second signal feature. For example, the processor 122 may locate the position of the first user in the physical space (for example, trilateral positioning) according to the amplitude feature of the first ultrasound signal received by the plurality of sound reception devices 121 to obtain the movement trajectory of the first user in the physical space. Then, the processor 122 may generate the second guidance message according to the movement trajectory.

Figure 5:
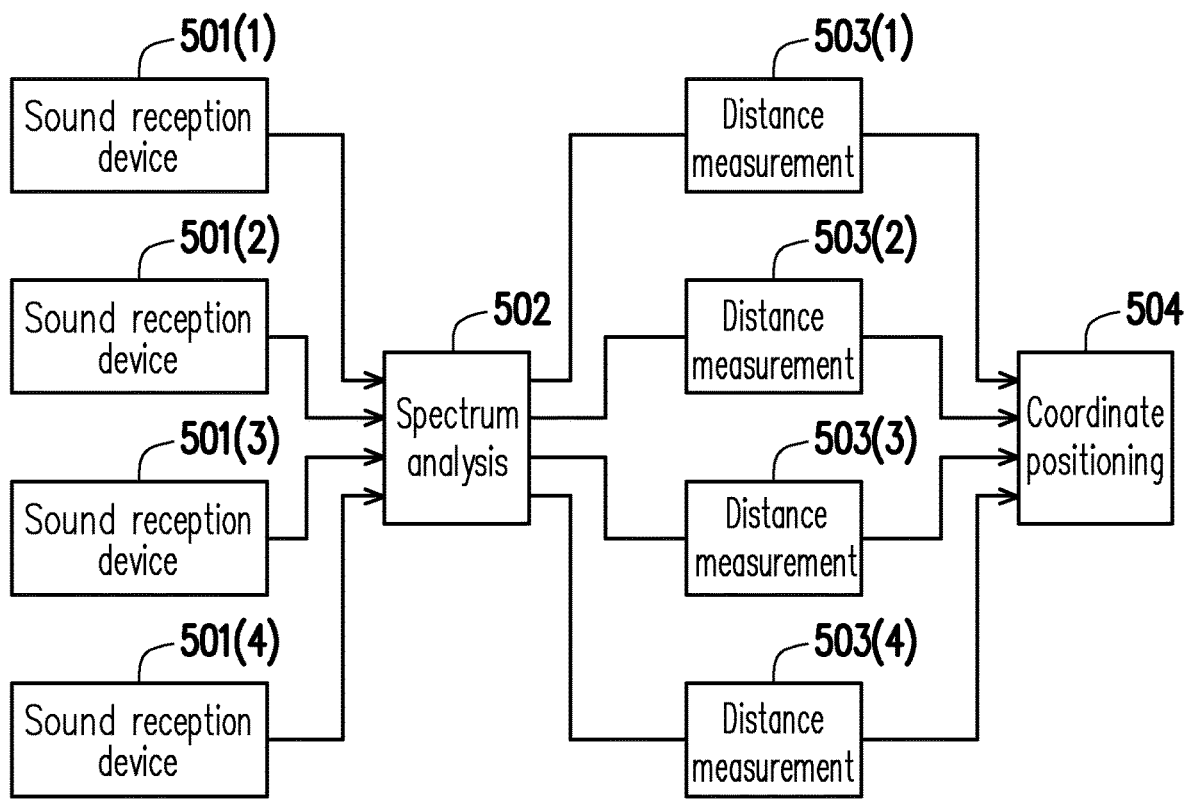
FIG. 5 is a schematic flowchart of locating a user's position in a physical space according to an embodiment of the invention.

More specifically, FIG. 5 is a schematic flowchart of locating a user's position in a physical space according to an embodiment of the invention. Referring to FIG. 5, it is assumed that the sound reception device 121 of FIG. 1 includes sound reception devices 501(1) to 501(4). All of the sound reception devices 501(1) to 501(4) may be used for receiving the first ultrasound signal. The processor 122 may perform a spectrum analysis 502 on the first ultrasound signals respectively received by the sound reception devices 501(1) to 501(4). In the spectrum analysis 502, the spectral features (i.e., the first signal features) of the first ultrasound signals may be used for identifying the first physical movement performed by the first user at the first time point and for generating the first guidance message. The operation of generating the first guidance message according to the spectral features of the first ultrasound signals is described in detail above, and the description is not repeated herein.

It should be noted that in the spectrum analysis 502, the amplitude feature (i.e., the second signal feature) of the first ultrasound signal may also be detected. According to the results of the spectrum analysis 502, distance measurements 503(1) to 503(4) may be performed to convert the amplitude feature of the first ultrasound signal detected by each of the sound reception devices 501(1) to 501(4) into the distance between the first user and each of the sound reception devices 501(1) to 501(4). For example, on the premise that the spatial coordinates of the sound reception device 501(i) are set in advance, the amplitude (i.e., signal strength) of the first ultrasound signal detected by the sound reception device 501(i) may be negatively correlated to the distance between the first ultrasound signal and the sound reception device 501(i). The distance measurement 503(i) may be used for calculating the distance between the first user and the sound reception device 501(i) via a conversion equation according to the results of the spectrum analysis 502 (i.e., the amplitude feature of the first ultrasound signal detected by each of the sound reception devices 501(1) to 501(4)). In particular, the conversion equation for performing the conversion between the amplitude and the distance of the signal may be designed according to practical requirements, and details are not repeated herein. Next, in a coordinate positioning 504, the distance between the first user and each of the sound reception devices 501(1) to 501(4) may be used for locating the coordinates of the first user in the physical space (for example, trilateral positioning), thereby tracking the movement trajectory of the first user in the physical space. Then, the movement trajectory (or the information of the position of the first user in the physical space) may be used for generating the second guidance message.

In an embodiment, when the movement teaching file (for example, the movement teaching file 306 of FIG. 3) is played, the first guidance message may be output by a multimedia device based on at least one of sound and video formats, so as to guide the second user to perform the first physical movement at the second time point via the first guidance message.

In an embodiment, when the movement teaching file (such as the movement teaching file 306 in FIG. 3) is played, the multimedia device may also generate a feedback message (also referred to as a third guidance message) according to the physical movement (i.e., the second physical movement) performed by the second user at the second time point. The third guidance message may be used for assisting the second user in evaluating the correctness of the performed second physical movement.

Figure 6:
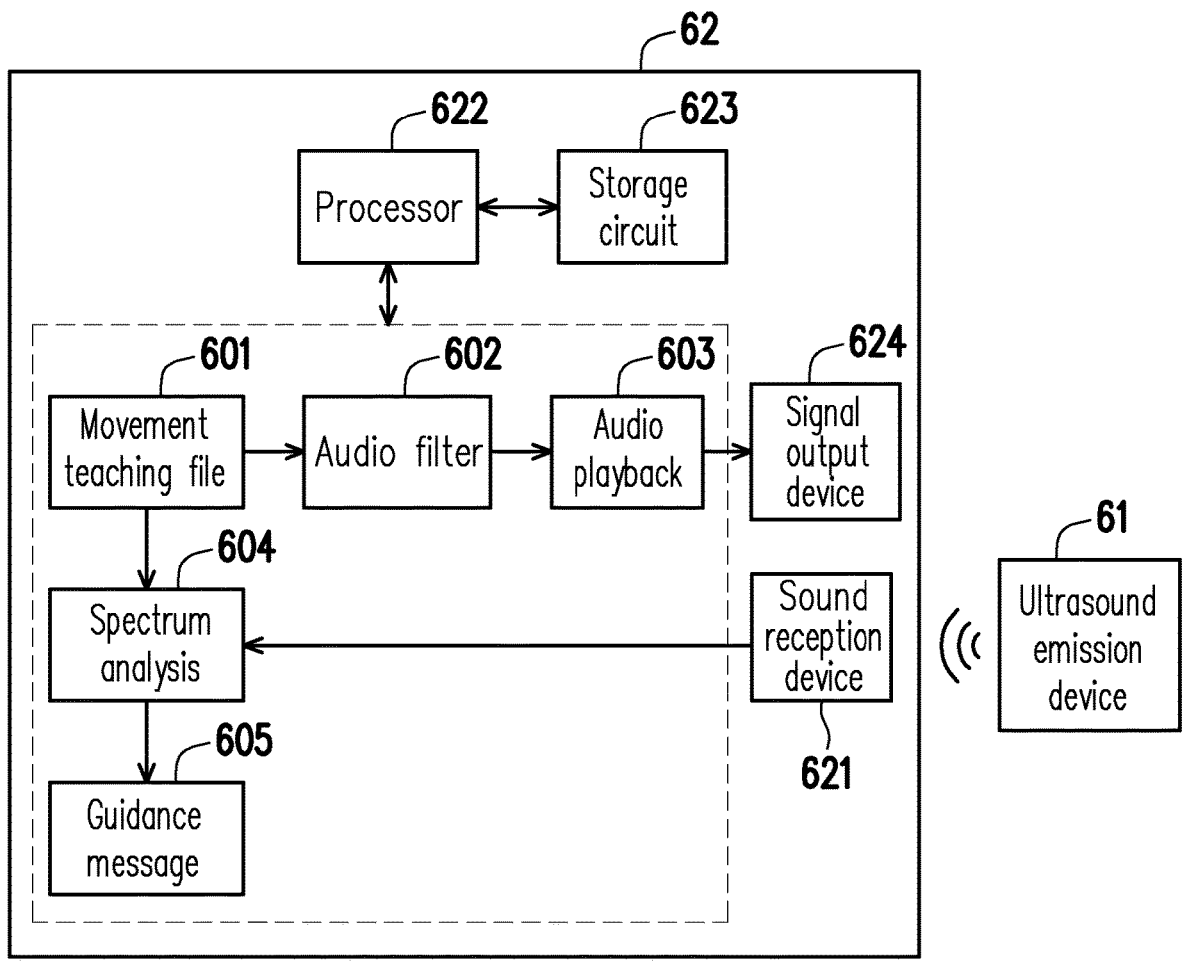
FIG. 6 is a schematic diagram of a system for movement guidance according to an embodiment of the invention.

FIG. 6 is a schematic diagram of a system for movement guidance according to an embodiment of the invention. Referring to FIG. 6, a system 60 for movement guidance includes an ultrasound emission device (also referred to as a second ultrasound emission device) 61 and a multimedia device 62. The ultrasound emission device 61 is suitable for being worn on the body of a user (i.e., a second user) and used for emitting an ultrasound signal (also referred to as a second ultrasound signal). For example, the ultrasound emission device 61 may include one or a plurality of ultrasound emitters. Each ultrasound emitter may be used for emitting an ultrasound signal having a specific frequency. For example, a plurality of ultrasound emitters (such as a third ultrasound emitter and a fourth ultrasound emitter) in the ultrasound emission device 61 are suitable to be worn at different positions on the body of the user (that is, the second user), and the plurality of ultrasound emitters in the ultrasound emission device 61 may be used for emitting ultrasound signals (i.e., second ultrasound signals) having different frequencies. It should be mentioned that, the ultrasound emission device 61 may be the same as or similar to the ultrasound emission device 11 of FIG. 1, and the manner of wearing the ultrasound emission device 61 on the body of the user is as provided in FIG. 2 or may be similar manners, and is not repeated herein.

The multimedia device 62 may include various electronic devices having multimedia signal transceiver and data processing functions such as smartphones, tablets, laptops, desktops, game consoles, smart headphones, smart speakers, or smart TVs, and the type of the multimedia device 62 is not limited thereto.

The multimedia device 62 may include a sound reception device 621, a processor 622, a storage circuit 623, and a signal output device 624. The sound reception device 621 may be used for receiving the second ultrasound signal. For example, the sound reception device 621 may include one or a plurality of microphones. It should be mentioned that, in FIG. 6, a movement teaching file 601, an audio filter 602, an audio playback 603, a spectrum analysis 604, and a guidance message 605 shown in the dotted box are actions performed by the processor 622 or the files stored in the storage circuit 623 (or other temporary storage circuits), wherein the actions performed by the processor 622 may be programmed or implemented in physical circuits.

The processor 622 is coupled to the sound reception device 621, the storage circuit 623, and the signal output device 624. The processor 622 may be responsible for all or part of the operation of the multimedia device 62. For example, the processor 622 may include a CPU or other programmable general or application-specific microprocessors, DSPs, programmable controllers, ASICs, PLDs, or other similar devices or a combination of these devices.

The storage circuit 623 is used for storing data. For example, the storage circuit 623 may include a volatile storage circuit and a non-volatile storage circuit. The volatile storage circuit is used for volatile storage of data. For example, the volatile storage circuit may include random-access memory (RAM) or similar volatile storage media. The non-volatile storage circuit is used for non-volatile storage of data. For example, the non-volatile storage circuit may include ROM, SSD, HDD, or similar non-volatile storage media.

The signal output device 624 is used for outputting a multimedia signal. For example, the signal output device 624 may include an audio output device such as an earphone or a speaker. Alternatively, in an embodiment, the signal output device 624 may further include a video output device such as a display.

The processor 622 may instruct the signal output device 624 to play background music in the form of sound and output the first guidance message in the form of sound or video according to the movement teaching file 601. In an embodiment, the processor 622 may also instruct the signal output device 624 to output the second guidance message in the form of sound or video according to the movement teaching file 601.

In an embodiment, the processor 622 may play the movement teaching file 601. For example, the movement teaching file 601 may be stored in the storage circuit 623. When the movement teaching file 601 is played, the audio playback 603 may perform audio processing procedures such as decoding the sound signal in the movement teaching file 601, and the signal output device 624 may output the background music and the first guidance message (and the second guidance message) according to the processing result of the audio playback 603. In addition, the processor 622 may also use a video player to perform video processing procedures such as decoding the video signals in the movement teaching file 601, and details are not repeated herein.

In an embodiment, during the playback of the movement teaching file 601, the sound reception device 621 may receive a second ultrasound signal emitted by the ultrasound emission device 61. The processor 622 may perform the spectrum analysis 604 on the second ultrasound signal to detect a signal feature (also referred to as a third signal feature) of the second ultrasound signal. In particular, the third signal feature may reflect the second physical movement performed by the second user at the second time point. The third signal feature may include a spectral feature of the second ultrasound signal. For example, the spectral feature of the second ultrasound signal may be used for describing the relative relationship between the frequency and time of the second ultrasound signal. Or, from another perspective, the spectral feature of the second ultrasound signal may reflect the amount of variation of the spectral feature of the second ultrasound signal between different time points. Moreover, in an embodiment, the third signal feature may also include an amplitude feature of the second ultrasound signal. For example, the amplitude feature of the second ultrasound signal may be used for describing the relative relationship between the amplitude (i.e., signal strength) of the second ultrasound signal and time, or to reflect the amount of variation of the amplitude of the second ultrasound signal between different time points. Then, the processor 622 may generate the guidance message 605 (i.e., a third guidance message) according to the third signal feature. In particular, the time period of playing the movement teaching file 601 is, for example, a training period.

For example, the processor 622 may evaluate the degree of similarity or difference between the second physical movement performed by the second user at the second time point and the first physical movement performed by the first user at the first time point according to the third signal feature. The processor 622 may generate the guidance message 605 according to the degree of similarity or difference. For example, the processor 622 may compare the third signal feature with the first signal feature and detect the difference between the third signal feature and the first signal feature. The difference may reflect the degree of similarity or difference between the second physical movement performed by the second user at the second time point and the first physical movement performed by the first user at the first time point. The processor 622 may generate the guidance message 605 according to the difference. For example, this difference may be expressed as an error rate. This error rate may be set to a larger value if the difference between the second physical movement and the first physical movement is larger. According to the error rate, the processor 622 may generate the guidance message 605. For example, the guidance message 605 may carry information of the error rate or information that may reflect the difference between the second physical movement and the first physical movement. For example, assuming that the similarity between the second physical movement and the first physical movement is about 80% (i.e., the error rate is 20%), the guidance message 605 may present, for example, "the movement similarity score is 80 points" or similar guidance or scoring information, so as to assist the second user in evaluating the correctness of the performed second physical movement. Moreover, the processor 622 may output via the signal output device 624 or another signal output device, or temporarily store the guidance message 605 in the storage circuit 623 for subsequent reference, and the invention is not limited in this regard.

In an embodiment, before the movement teaching file 601 is played, the processor 622 may filter out the signal content of the first ultrasound signal from the movement teaching file 601 via the audio filter 602. After the first ultrasound signal is filtered out from the movement teaching file 601, the processor 622 may play the filtered movement teaching file 601, so as to output the background music and the first guidance message (and the second guidance message) via the signal output device 624. In other words, by pre-filtering the first ultrasound signal in the movement teaching file 601 before the movement teaching file 601 is played, the first ultrasound signal may be prevented from being output by the signal output device 624 during the playback of the movement teaching file 601. Accordingly, the background music output according to the movement teaching file 601 may be prevented from being interfered by the synchronously output first ultrasound signal, and/or the signal quality of the second ultrasound signal received during the playback of the movement teaching file 601 may be improved.

Figure 7:
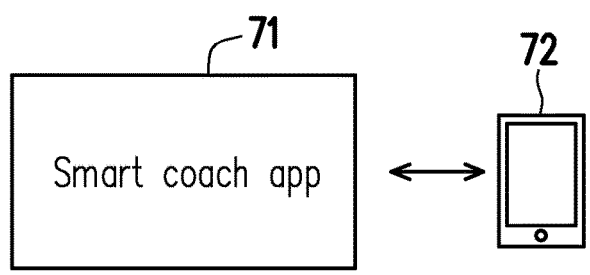
FIG. 7 is a schematic diagram of a smart coach application according to an embodiment of the invention.

FIG. 7 is a schematic diagram of a smart coach application according to an embodiment of the invention. Referring to FIG. 7, in an embodiment, an application (also referred to as a smart coach application) 71 may be downloaded and installed in an electronic device 72. The electronic device 72 may include the electronic device 12 of FIG. 1 or the multimedia device 62 of FIG. 2. For example, the application 71 may be stored in the storage circuit of the electronic device 72. The processor of the electronic device 72 may run the application 71 to perform all or at least part of the functions mentioned in the above embodiments, including recording teaching materials, reading teaching materials, spectrum analysis, audio synthesis, audio playback, receiving sound signals, outputting guidance messages, and scoring user movement, etc. The relevant operation details are all provided above, and are not repeated herein.

In an embodiment, a cloud server may also be used for performing functions such as spectrum analysis and generation of guidance messages mentioned in the above embodiments. In an embodiment, the cloud server may include a communication interface and a processor. The communication interface is used for communicating with the electronic device 11 of FIG. 1, the multimedia device 62 of FIG. 6, or the electronic device 72 of FIG. 7 to perform remote data transmission. For example, the communication interface may be used for communicating with the sound reception device 11 of FIG. 1. After the first ultrasound signal and the background sound signal are received, the sound reception device 11 may transmit the first ultrasound signal and the background sound signal to the processor of the cloud server via the communication interface of the cloud server. In an embodiment, at least part of the signal processing and/or data processing operations performed by the processor 122 of FIG. 1 and/or the processor 622 of FIG. 6 in the above embodiments may instead be performed by the processor of the cloud server (for example, performing spectrum analysis to generate the first guidance message, the second guidance message, the movement teaching file, and the third guidance message, etc.) Then, a terminal device (e.g., the multimedia device 62 of FIG. 6) may download the desired movement teaching file from the server and play it for the user (e.g., the second user) to conduct self-training and self-evaluation of the learning effect. The relevant operation details are provided above, and are not repeated herein.

Figure 8:
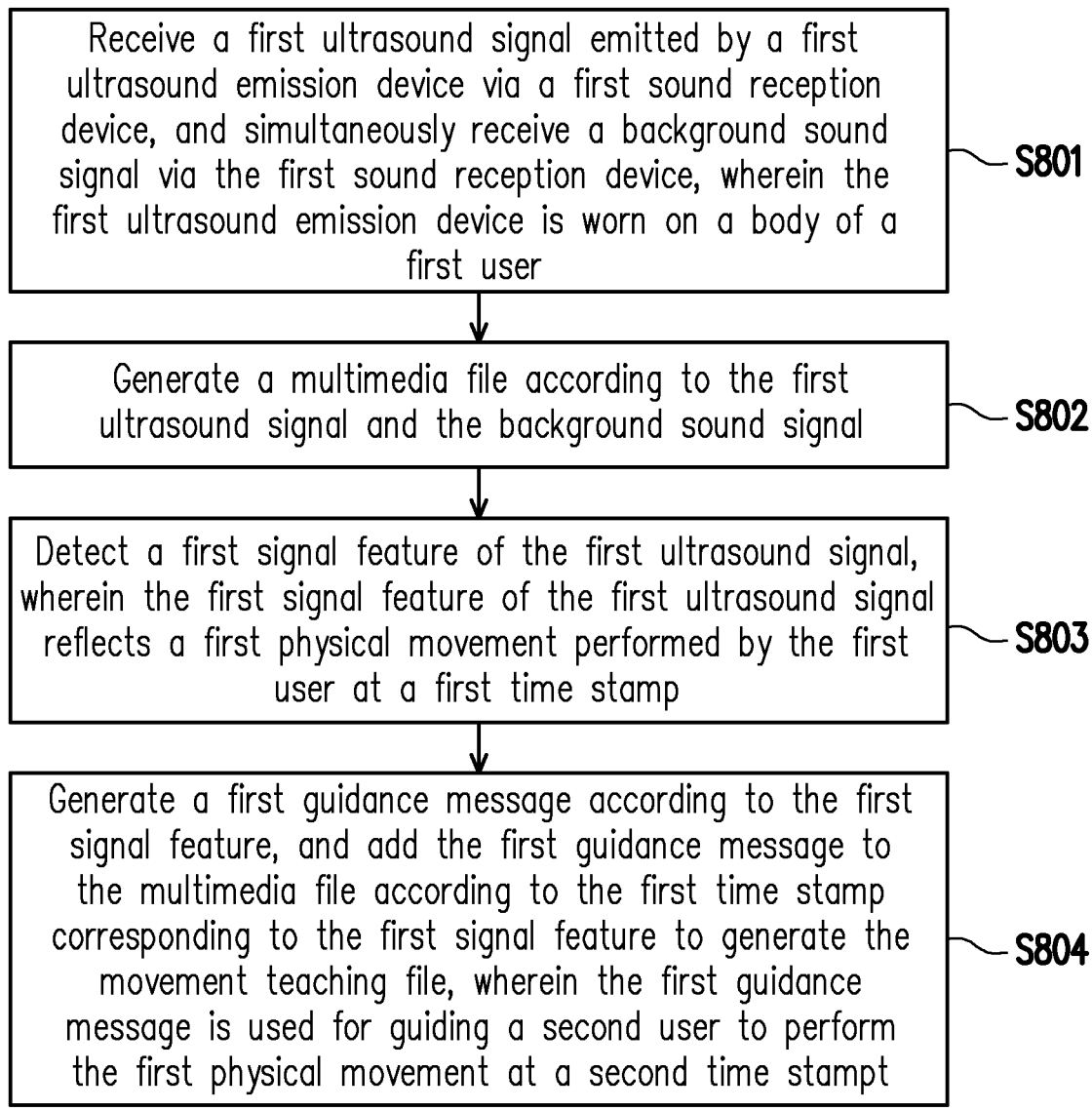
FIG. 8 is a flowchart of a method for movement guidance according to an embodiment of the invention.

FIG. 8 is a flowchart of a method for movement guidance according to an embodiment of the invention. Referring to FIG. 8, in step S801, a first ultrasound signal emitted by at least one first ultrasound emission device is received via at least one first sound reception device, and a background sound signal is simultaneously received via the at least one first sound reception device, wherein the at least one first ultrasound emission device is worn on a body of a first user. In step S802, a multimedia file is generated according to the first ultrasound signal and the background sound signal. In step S803, a first signal feature of the first ultrasound signal is detected, wherein the first signal feature reflects a first physical movement performed by the first user at a first time point. In step S804, a first guidance message is generated according to the first signal feature, and the first guidance message is added to the multimedia file according to the first time point corresponding to the first signal feature to generate a movement teaching file, wherein the first guidance message is used for guiding a second user to perform the first physical movement at a second time point.

However, each step in FIG. 8 is as described in detail above, and is not repeated herein. It should be mentioned that, each step in FIG. 8 may be implemented as a plurality of program codes or circuits, and the invention is not limited thereto. Moreover, the method of FIG. 8 may be used with the above exemplary embodiments, and may also be used alone, and the invention is not limited thereto.

Based on the above, by analyzing the signal features of the first ultrasound signal to sense the movement of the first user (e.g., a coach), the recording of the movement teaching file and the automatic addition of the movement guidance message may be completed without starting a video recording program. In this way, the personal privacy of the coach may be protected, the recording cost of the movement teaching file may be reduced, and the learner may be guided to perform movements during the self-training process thereof. Second, by analyzing the signal features of the second ultrasound signal to evaluate the correctness of the training movement performed by the second user, movement monitoring and scoring of the learner may be performed without the coach being present. Thereby, the self-training efficiency of the learner is further improved. Moreover, in the invention, the movement monitoring and scoring of the learner are also performed via the analysis of the ultrasound signal (not via an image lens) to protect the personal privacy of the learner.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. Moreover, these claims may refer to use "first", "second", etc., following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A method for movement guidance, comprising:
receiving a first ultrasound signal emitted by at least one first ultrasound emission device via at least one first sound reception device, and simultaneously receiving a background sound signal via the at least one first sound reception device, wherein the at least one first ultrasound emission device is worn on a body of a first user;
generating a multimedia file according to the first ultrasound signal and the background sound signal;
detecting a first signal feature of the first ultrasound signal, wherein the first signal feature reflects a first physical movement performed by the first user at a first time point; and
generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

2. The method for movement guidance of claim 1, wherein the first signal feature comprises a spectral feature of the first ultrasound signal.

3. The method for movement guidance of claim 2, wherein the step of generating the first guidance message according to the first signal feature comprises:
determining that the first physical movement performed by the first user at the first time point is a first movement in response to the first signal feature meeting a first condition; and
determining that the first physical movement performed by the first user at the first time point is a second movement in response to the first signal feature meeting a second condition, wherein the first condition is different from the second condition, and the first movement is different from the second movement.

4. The method for movement guidance of claim 1, wherein the at least one first ultrasound emitter comprises a first ultrasound emitter and a second ultrasound emitter, the first ultrasound emitter and the second ultrasound emitter are worn at different positions on the body of the first user, the first ultrasound emitter is used for emitting an ultrasound signal having a first frequency, the second ultrasound emitter is used for emitting an ultrasound signal having a second frequency, and the first frequency is different from the second frequency.

5. The method for movement guidance of claim 1, further comprising:
detecting a second signal feature of the first ultrasound signal, wherein the second signal feature reflects a change in a position of the first user in a physical space; and
generating a second guidance message according to the second signal feature, wherein the second guidance message is used for guiding the second user to move in a specific direction.

6. The method for movement guidance of claim 5, wherein the second signal feature comprises an amplitude feature of the first ultrasound signal.

7. The method for movement guidance of claim 6, wherein the step of generating the second guidance message according to the second signal feature comprises:
tracking a movement trajectory of the first user in the physical space according to the second signal feature; and generating the second guidance message according to the movement trajectory.

8. The method for movement guidance of claim 1, further comprising:
outputting the first guidance message via a signal output device based on at least one form of a sound and an image when the movement teaching file is played, so as to guide the second user to perform the first physical movement at the second time point via the first guidance message.

9. The method for movement guidance of claim 1, further comprising:
receiving a second ultrasound signal emitted by at least one second ultrasound emission device via at least one second sound reception device when the movement teaching file is played, wherein the at least one second ultrasound emission device is worn on a body of the second user;
detecting a third signal feature of the second ultrasound signal, wherein the third signal feature reflects a second physical movement performed by the second user at the second time point; and
generating third guidance information according to the third signal feature, wherein the third guidance information is used for assisting the second user to evaluate a correctness of the second physical movement.

10. The method for movement guidance of claim 9, further comprising:
filtering out information of the first ultrasound signal from the movement teaching file before the movement teaching file is played; and
playing the filtered movement teaching file after the information of the first ultrasound signal is filtered out from the multimedia file.

11. A system for movement guidance, comprising:
at least one first ultrasound emission device suitable to be worn on a body of a first user and used for emitting a first ultrasound signal;
at least one first sound reception device used for receiving the first ultrasound signal and a background sound signal; and
a processor coupled to the at least one first sound reception device and used for:
generating a multimedia file according to the first ultrasound signal and the background sound signal;
detecting a first signal feature of the first ultrasound signal, wherein the first signal feature reflects a first physical movement performed by the first user at a first time point; and
generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

12. An electronic device, comprising:
at least one first sound reception device used for receiving a first ultrasound signal emitted by at least one first ultrasound emission device and simultaneously receiving a background sound signal, wherein the at least one first ultrasound emission device is worn on a body of a first user; and
a processor coupled to the at least one first sound reception device and used for:
generating a multimedia file according to the first ultrasound signal and the background sound signal;
detecting a first signal feature of the first ultrasound signal, wherein the first signal feature reflects a first physical movement performed by the first user at a first time point; and
generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

13. A server, comprising:
a communication interface used for communicating with at least one first sound reception device;
a processor coupled to the communication interface,
wherein the at least one first sound reception device is used for receiving a first ultrasound signal emitted by at least one first ultrasound emission device and synchronously receiving a background sound signal and transmitting the first ultrasound signal and the background sound signal to the processor via the communication interface, and the at least one first ultrasound emission device is worn on a body of a first user, and
the processor is used for:
generating a multimedia file according to the first ultrasound signal and the background sound signal;
detecting a first signal feature of the first ultrasound signal, wherein the first signal feature reflects a first physical movement performed by the first user at a first time point; and
generating a first guidance message according to the first signal feature, and adding the first guidance message to the multimedia file according to the first time point corresponding to the first signal feature to generate a movement teaching file, wherein the first guidance message is used for guiding a second user to perform the first physical movement at a second time point.

* * * * *